United States Patent [19]
Nemoto et al.

[11] Patent Number: 5,552,322
[45] Date of Patent: Sep. 3, 1996

[54] DNA BASE SEQUENCER

[75] Inventors: Ryozi Nemoto, Honzyo; Yoshinori Mishina, Saitama-ken, both of Japan

[73] Assignee: Hitachi Electronics Engineering Co., Ltd., Tokyo, Japan

[21] Appl. No.: 313,912

[22] Filed: Sep. 28, 1994

[30] Foreign Application Priority Data

Sep. 28, 1993 [JP] Japan .................................. 5-264320

[51] Int. Cl.⁶ .................................................. C12M 1/34
[52] U.S. Cl. ...................... 435/287.2; 204/612; 204/618; 356/344; 422/82.08; 422/131
[58] Field of Search ........................... 204/182.8, 299 R; 356/344; 422/82.08, 131, 187; 435/291; 935/86, 88

[56] References Cited

U.S. PATENT DOCUMENTS

| | | | |
|---|---|---|---|
| 4,927,268 | 5/1990 | Carr et al. | 356/336 |
| 5,112,736 | 5/1992 | Caldwell et al. | 435/6 |
| 5,257,086 | 10/1993 | Fateley et al. | 356/328 |
| 5,297,288 | 3/1994 | Hemminger et al. | 395/700 |
| 5,405,783 | 4/1995 | Pirrung et al. | 436/518 |

FOREIGN PATENT DOCUMENTS

| | | |
|---|---|---|
| 0504943 | 3/1992 | European Pat. Off. . |
| 3812899 | 4/1988 | Germany . |
| 4011730A | 4/1990 | Germany . |
| 63-21556 | 1/2988 | Japan . |

WO87/07719 12/1987 WIPO .

OTHER PUBLICATIONS

Biotechnology, Vol. 10, No. 1, Jan. 1992, "High Speed Automated DNA Sequencing in Ultrathin Slab Gels", Kostichka et al, pp. 78–81.

Trac: Trends in Analytical Chemistry, May 13, 1994, No. 5, "The Pigtailing Approach to Optical Detection in Capillary Electrophoresis", Bruno et al, pp. 190–198.

*Primary Examiner*—David A. Redding
*Attorney, Agent, or Firm*—Fay, Sharpe, Beall, Fagan, Minnich & McKee

[57] ABSTRACT

The improved DNA base sequencer comprises a flat plate type gel electrophoretic means that has a multiple of tracks for electrophoresing DNA fragments and which is held in a vertical position, a light exciting laser light applying means that applies laser light to the respective tracks in said electrophoretic means from one lateral side thereof in such a way that it crosses said tracks at right angles, and a fluorescence detecting means that detects the fluorescence as generated from the DNA fragments illuminated with the laser light and which converts the detected fluorescence to an electric signal, and it is characterized in that the fluorescence detecting means comprises an index-distributed lens array, a filter and a solid-state imaging device such as a CCD line sensor. This apparatus uses light-receiving optics that does not include a large and expensive optical device such as an image intensifier and which yet is capable of efficient fluorescence detection without "smiling" and other adverse effects.

5 Claims, 4 Drawing Sheets

5,552,322

DNA BASE SEQUENCER

BACKGROUND OF THE INVENTION

This invention relates to a DNA base sequencer, or an apparatus for determining the base sequences of DNA. More particularly, this invention relates to an apparatus with which the base sequences of DNA can be determined by fluorescent labelling in an efficient and rapid manner.

Gel electrophoresis is practiced extensively as a technique for determining the base sequences of DNA and other proteins. Conventionally, the sample to be subjected to electrophoresis is labelled with a radioisotope for analysis but this method has had the problem of being painstaking and time-consuming. Furthermore, the use of radioactive substances always calls for utmost safety and management and analysis cannot be performed in areas other than facilities that clear certain regulations. Under the circumstances, a method that uses fluorophores to label the sample and which detects fluorescences as emitted upon irradiation with light is being reviewed.

In this method, fluorophore-labelled DNA fragments are caused to migrate through a gel and a light excitation portion and a photodetector are provided for each electrophoresis track in an area 15–20 cm below the start point of electrophoresis. The DNA fragments are assayed as they pass through the line connecting the light excitation portion and the photodetector. A typical procedure of the method is described below. First, using as template the DNA chain to be determined for its base sequence, DNAs of various lengths with known terminal base species are replicated by a method involving an enzymatic reaction (the dideoxy method). Then, the replicated DNAs are labelled with a fluorophore. Stated more specifically, there are prepared a group of adenine (A) fragments, a group of cytosine (C) fragments, a group of guanine (G) fragments and a group of thymine (T) fragments, all being labelled with a fluorophore. A mixture of these fragment groups is injected into separate lane grooves in an electrophoretic gel and, thereafter, a voltage is applied at opposite ends of the gel. Since DNA is a chained polymer with negative charges, it will move across the gel at a rate in inverse proportion to its molecular weight. The shorter the DNA chain (the smaller its molecular weight), the faster will it move and vice versa; this is the principle behind the fractionation of DNA by molecular weight.

Japanese Laid-Open Patent Application (Kokai) No. 21556/1988 teaches a DNA base sequencer that is adapted in such a way that a line on the gel in an apparatus for electrophoresis at which laser light is applied and the direction in which photodiodes are arranged are both perpendicular to the direction in which DNA fragments migrate in the apparatus. The setup of this apparatus is shown schematically in FIG. 6. An electrophoresis plate 74 comprises a gel (typically a polyacrylamide gel) held between two glass plates. The electrophoresis plate has an overall thickness of up to about 10 mm but the thickness of the gel electrolyte layer itself is less than about 1 mm. The upper end of the gel electrolyte layer is comb-shaped and located slightly below the upper end of the plate 74. Fluorophore-labelled DNA fragments to be assayed are injected into grooves 75 corresponding to the teeth of the comb.

In the apparatus shown in FIG. 6, a laser beam emitted from a light source 70 is reflected by a mirror 72 and launched horizontally from one side of the plate 74 at a predetermined point on the gel. As the fluorophore-labelled DNA fragments migrating through the gel pass through the irradiated region, they will fluoresce successively. The horizontal position of fluorescence emission tells the species of a particular terminal base, the time difference from the start of migration tells the length of a particular fragment, and the emission wavelength identifies the sample under assay. The fluorescence from each electrophoresis track is condensed by a lens 78 to focus at a light-receiving area in an image intensifier 80. The received signal is amplified and converted to an electric signal in a photodiode array 84 for the purpose of various measurements. The results of measurements are processed with a computer so that the sequences of the individual DNA fragments are calculated to determine the base sequence of the DNA at issue.

The apparatus shown in FIG. 6 uses an image intensifier camera in the light-receiving optics. The image intensifier camera is not only very expensive but also comparatively large as an optical device. Under the circumstances, an apparatus of the design shown in FIG. 7 was developed, which had an individual fluorescence detecting means provided in the detection position of each electrophoresis track 88. Each fluorescence detecting means consisted of a filter 100, a condensing lens 110 and a light-receiving device 120. Filter 100 is provided for rejecting the excited light and the background light so that fluorescence is transmitted selectively. Condensing lens 110 is used for insuring that the filtered fluorescence is focused at the light-receiving plane of the device 120. The light-receiving device 120 is typically a photodiode composed of a silicon crystal having a pn junction.

A problem with the apparatus shown in FIG. 7 is that electrophoresis tracks are sensitive to external factors including temperature conditions, temperature profile and gel dissolution, so that the tracks deviate progressively from the linear state and as they run downward, the tracks become curved progressively until they occasionally shift either to the right or to the left. This shift of electrophoresis tracks is generally called "smiling". If smiling occurs, the position where fluorescence is emitted in response to the entrance of laser excited light into the DNA sample will deviate from the position where the fluorescence detecting means is provided; as a result, the efficiency of fluorescence detection drops and the precision with which the base sequences of DNA can be determined will decrease accordingly.

A further problem with the apparatus shown in FIG. 7 originates from the use of the condensing lens in each fluorescence detecting means. That is, the reduced fluorescent image causes an interference between adjacent electrophoresis tracks and it occasionally becomes difficult to achieve full separation of the fluorescent image waveform formed in one electrophoresis track from the waveform formed in an adjacent track, whereby the resolving power of the apparatus is lowered. To maintain a reasonable resolving power, the distance between electrophoresis tracks has to be increased but then the number of samples that can be analyzed at a time decreases, so does the throughput of the analysis.

SUMMARY OF THE INVENTION

The present invention has been accomplished under these circumstances and has as an object providing a DNA base sequencer using light-receiving optics that does not include a large and expensive optical device such as an image intensifier and which yet is capable of efficient fluorescence detection without smiling and other adverse effects.

To attain this object, the present invention adopts an improved fluorescence detection means that consists of an index-distributed lens array, a filter and a solid-state imaging device.

The index-distributed lens array, filter and solid-state imaging device which constitute the fluorescence detection means extend from one end to the other end of the electrophoresis plate with which it is to be used and this design feature assures effective fluorescence detection even if the sample of interest "smiles" during electrophoresis.

Unlike the conventional camera leans, the index-distributed lens array is in close proximity with the electrophoresis plate for imaging the fluorescent image and this insures uniform signal levels to be attained between the center and either end of the plate. As a result, the uniformity of S/N ratio is improved and one can read the length of bases in lanes in the marginal portions of the plate as precisely as in lanes at the center and nearby areas. Since index-distributed lenses are disposed in an array, adjacent lens images will overlap, whereby 1:1 erecting imaging optics is provided in the lens mounting area. This contributes to the elimination of the imaging optics interference between adjacent electrophoresis tracks which has been a common problem with the conventional camera lens.

THE PREFERRED EMBODIMENTS OF THE INVENTION

The present invention is described below in greater detail with reference to FIGS. 1–5.

Figure 1:
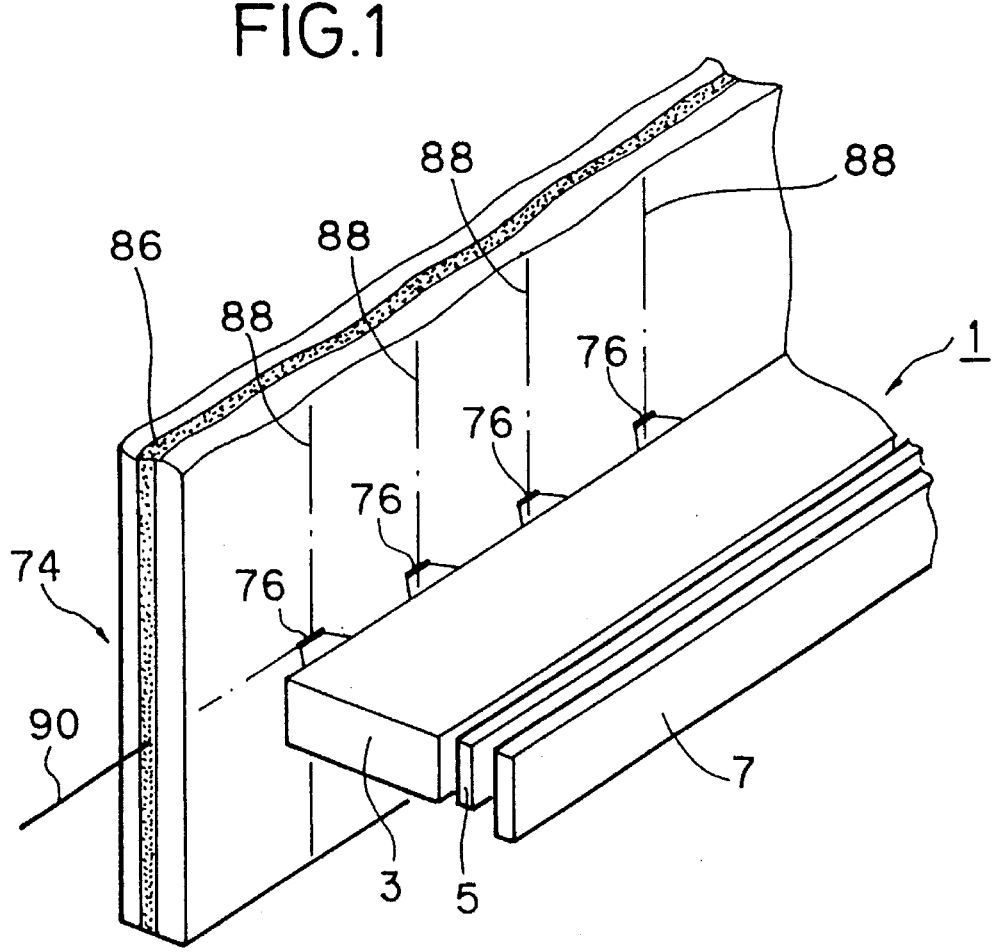
FIG. 1 is a perspective view showing schematically the partial structure of the fluorescence detecting means used with the DNA base sequencer of the invention.

FIG. 1 is a perspective view showing schematically the partial structure of fluorescence detecting means that is used with the DNA base sequencer of the invention and which is generally indicated by reference numeral 1. The fluorescence detecting means consists basically of an index-distributed lens array 3, a filter 5, and a solid-state imaging device such as a CCD (charge-coupled device) line sensor 7. DNA fragments 76 are migrating downward along respective electrophoresis tracks 88 on a gel electrolyte layer 86 in an electrophoresis plate 74, when they are illuminated with laser light 90 from one lateral side of the gel electrolyte layer, whereupon fluorescence is emitted from the illuminated DNA fragments. The emitted fluorescence is launched into the index-distributed lens array 3 and passes through it to enter the filter 5, which cuts off the background light or any stray light that has wavelengths other than those of the fluorescent components. The fluorescent light that has passed through the filter is picked up by the CCD line sensor 7 for conversion to electric signals. In addition to the CCD line sensor, a MOS transistor array or a photodiode array may also be used as the solid-state imaging device with equal results.

Figure 2:
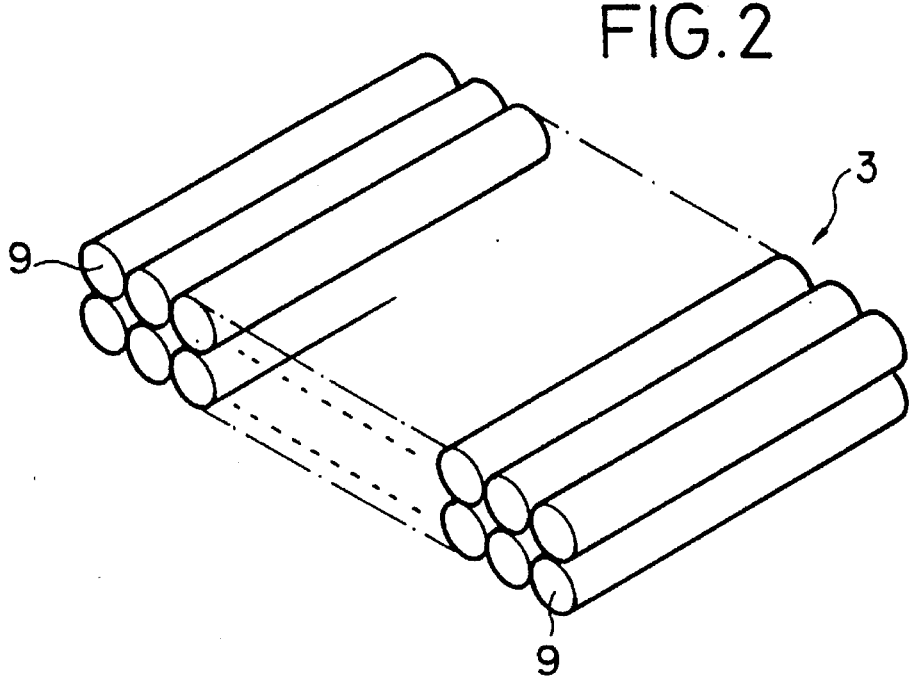
FIG. 2 is an enlarged perspective view showing schematically the index-distributed lens array for use in the invention as part of the fluorescence detecting means.

FIG. 2 is an enlarged perspective view showing schematically the index-distributed lens array 3. Each of the index-distributed lenses 9 used in the invention is also known as a "Selfoc lens" which is a cylindrical lens having a refractive index distribution in the radical direction. The "Selfoc lens" to be used in the invention is commercially available under code number SLA-20B (F0.96) and has a diameter of about 1 mm with a length of about 12–13 mm. Selfoc lenses can be used as a single-row array. In the embodiment shown in FIG. 2, the lens array 3 consists of an upper and a lower row, each being composed of 200 lenses amounting to a total of 400 lenses. The Selfoc lenses are arrayed in two rows for the purpose of achieving a higher resolution by allowing more light to be accepted by the lenses. If the Selfoc lenses are arrayed in two rows, the numerical aperture of the lens optics is increased to enable the detection of weak fluorescence. If desired, Selfoc lenses may be stacked in three or more rows. Needless to say, lenses 9 are supported by a suitable enclosure or retainer so that they are held together in the form of lens array 3.

The filter 5 may be selected as appropriate to the kinds of fluorescence marker and laser light source (i.e., the wavelength of laser light) used. The DNA base sequencer of the invention uses an argon ion laser as the laser light source. Hence, the laser light used in the invention has a wavelength of about 488 nm. The sequencer also uses FITC as the fluorophore for labelling DNA fragments. When illuminated with the laser light having the above-mentioned wavelength, FITC emits fluorescence at a wavelength of about 515 nm. Hence, the filter 5 is preferably of such a type that only fluorescence having the wavelength 515 nm is transmitted while the background light or any stray light having wavelengths other than 515 nm is effectively rejected. An example of such filters is one that is coated with a dielectric multi-layered film. The thickness of the filter 5 is not limited to any particular value; however, generally speaking, thicknesses in the range from 1 to 5 mm are used with advantage.

CCD line sensor 7 has a plurality of CCDs arranged side by side in a linear fashion and it is also used in the photoelectric transducer portion of scanning optics in OCRs or facsimiles. The CCDs to be used in the invention are not limited to any particular types and TCD 109AC (pixel size: 6×65 µm) may be used with advantage. The distance between the upper and lower edges of the CCD line sensor (namely, the width as measured in the electrophoresing direction) is not limited to any particular value; however, values no more than 85 µm are generally preferred. In the early stage of electrophoresis, DNA fragments separate sharply enough to facilitate their detection; but toward the end of electrophoresis, the separability of DNA fragments decreases progressively until they migrate collectively. If the distance between the upper and lower edges of the CCD line sensor is not more than 85 µm, DNA fragments can be detected individually even if they migrate collectively. If only one CCD line sensor is used, it functions as a one-dimensional sensor; on the other hand, if two or more CCD line sensors are stacked in a corresponding number of rows, a two-dimensional area sensor is realized.

Figure 3:
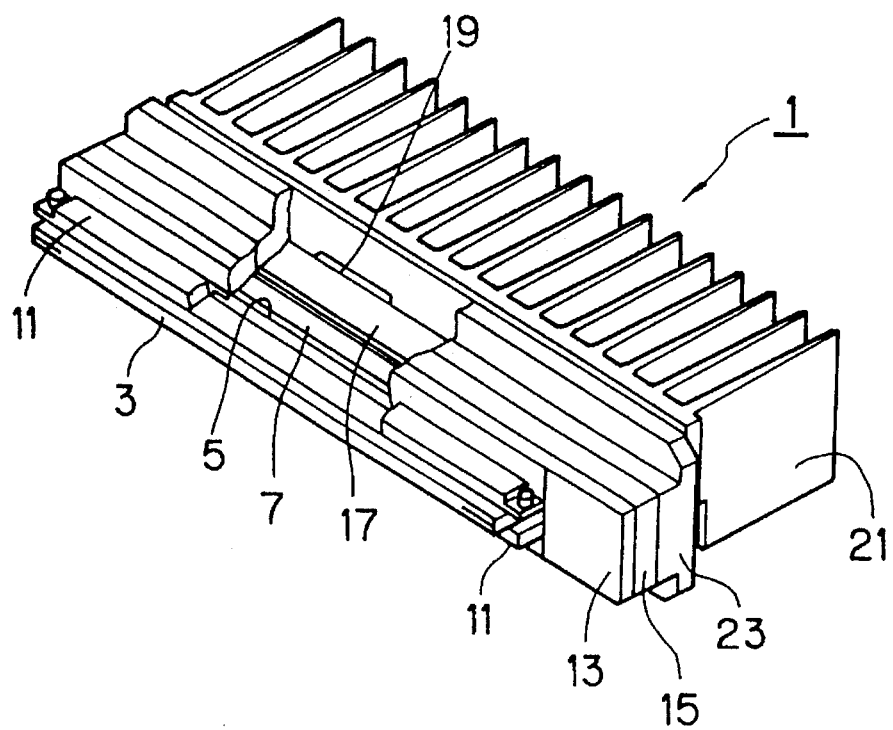
FIG. 3 is a perspective view showing, with part taken away, an example of the assembly of the fluorescence detecting means shown in FIG. 1.

FIG. 3 is a perspective view showing, with part taken away, an example of the assembly of the fluorescence detecting means 1 shown in FIG. 1. As shown in FIG. 3, the index-distributed lens array 3 is held between suitable fixing plates 11. One of the fixing plates 11 is secured to a filter mount 13, in which the filter 5 is installed. Adjacent to and in close contact with the filter mount 13, there is provided a CCD mount 15, in which the CCD line sensor 7 is disposed. When driven, the CCDs generate heat and the dark current will increase to produce noise, hence, causing adverse effects such as a reduced S/N ratio. To avoid these problems, a uniform heating zone 17 is provided in contact with the CCD line sensor 7 and an electronic cooler/heater 19 such as a Peltier device is provided in contact with the heating zone 17. The CCD line sensor is preferably maintained at a temperature within the range from about 10° C. to about 15° C. by means of the Peltier device 19. A heat sink 21 is secured to the electronic cooler heater 19 so as to improve its heat dissipation characteristics. The heating zone 17 and the electronic cooler/heater 19 are both held by means of a cooling mount 23. As is generally the case, the CCDs are mounted on a CCD substrate or board but this portion is omitted from FIGS. 3 and 4 for clarity.

Figure 4:
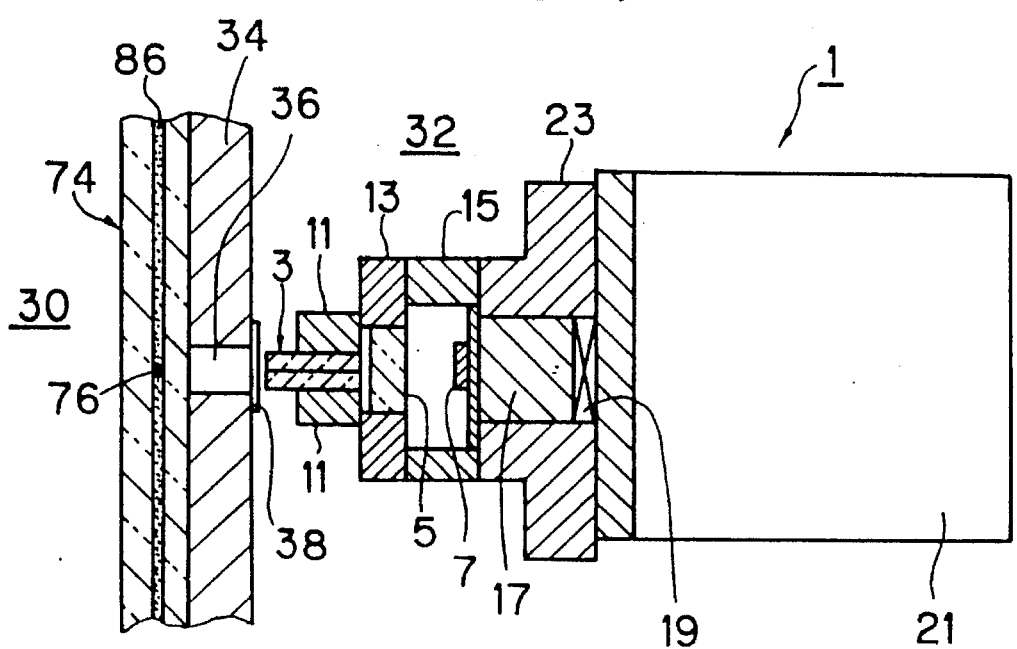
FIG. 4 is a sectional view showing schematically the fluorescence detecting means assembly of FIG. 3 as it is mounted on the DNA base sequencer.

A further discussion is made with reference to FIG. 4, which is a sectional view showing schematically the fluorescence detecting means assembly 1 of FIG. 3 as it is mounted on the DNA base sequencer. The DNA base sequencer of the invention comprises basically a dark compartment 30 containing an electrophoresis plate 74 and a measurement compartment 32 containing the fluorescence detecting means assembly 1. The dark compartment 30 is separated from the measurement compartment 32 by a partition 34. The partition 34 has an opening 36 in the position corresponding to the point of entrance of laser light into electrophoresis plate 74 so that excited fluorescence is effectively guided toward the measurement compartment 32. An airtinghtness providing glass plate 38 is secured to the end of the opening 36 where it faces the measurement compartment 32 in order to assure that the moisture or heat in the dark compartment 30 will not enter the measurement compartment through the opening. The electrophoresis plate 74 is detachable and retained in a vertical erect position so that it makes close contact with the partition 34. The distance from the point of incidence of laser light 76 on the electrophoresis plate 74 to the front end of the Selfoc lens array is not limited to any particular value but a value of about 15 mm is selected in the embodiment under discussion. The distance from the rear end of the Selfoc lens array to the surface of the CCD line sensor 7 also is not limited to any particular value but a value of 15 mm is selected in the embodiment under discussion. The distance from the point 76 to the front end of the Selfoc lens array may or may not be the same as the distance from the rear end of the Selfoc lens array to the surface of the CCD line sensor 7. Preferably, the two distances are the same because the Selfoc lenses which have a magnification of unity are preferably provided with the same volume of gaps both ahead and behind the lenses.

Figure 5:
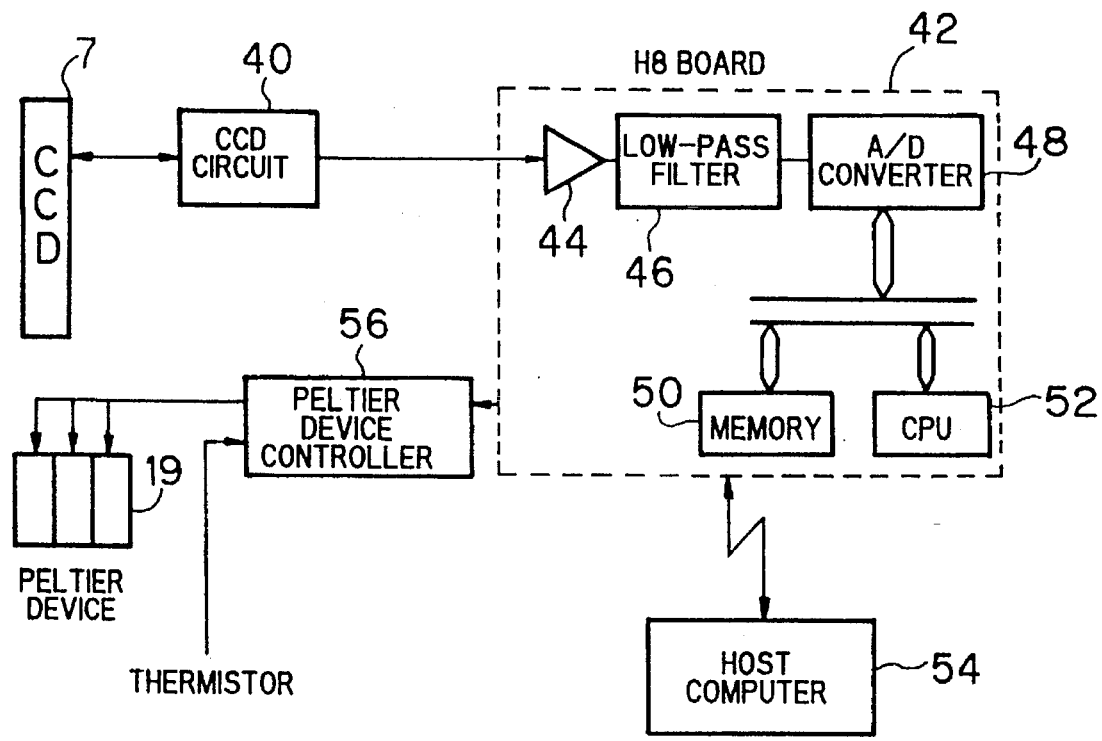
FIG. 5 is a block diagram of a signal processing system including a CCD circuit.
Figure 6:
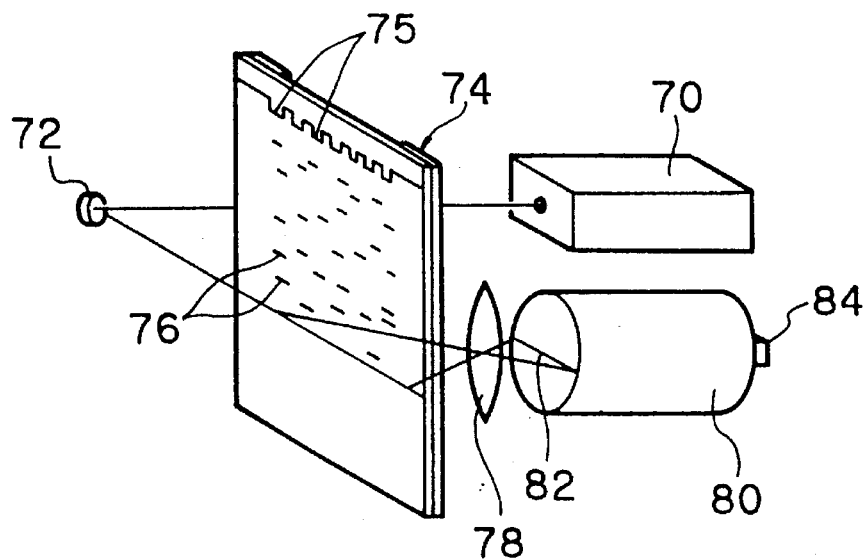
FIG. 6 is a sketch showing schematically the setup of the DNA base sequencer disclosed in Japanese Laid-Open Patent Application (kokai) No. 21556/1988.
Figure 7:
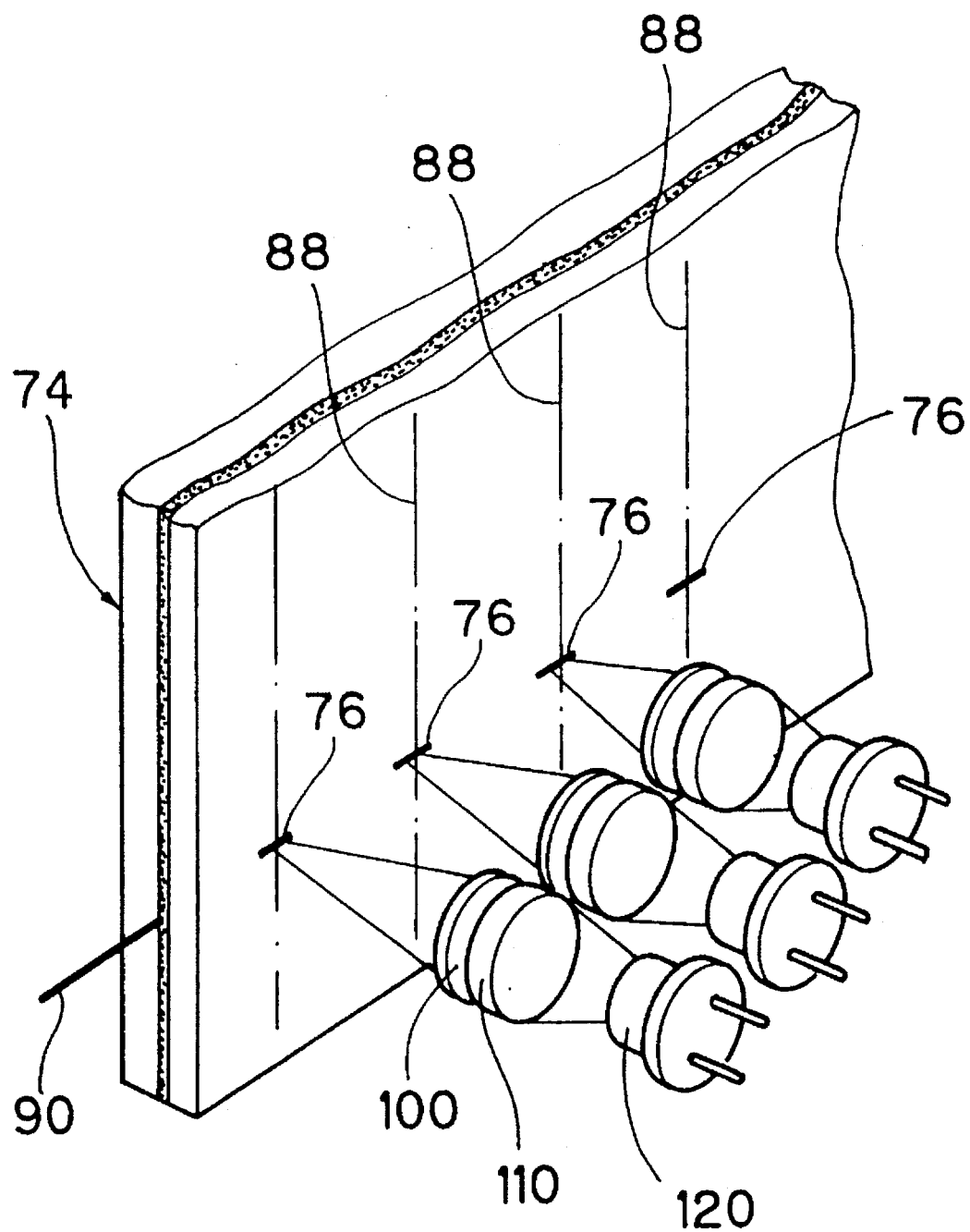
FIG. 7 is a sketch showing schematically an example of the DNA base sequencer in which fluorescence detecting means that consists of a filter, a condensing lens and a light-receiving device is provided for each of the electrophoresis tracks on an electrophoresis plate.

FIG. 5 is a block diagram of a signal processing system including a CCD circuit. The CCD line sensor 7 is driven with the CCD circuit indicated by 40. The contents of the CCD circuit 40 are essentially the same as those of a known conventional CCD drive circuit and comprise a timing controller, a timing generator circuit, a multiplexer, etc. An analog output as received by the CCD line sensor 7 and subsequently processed in the CCD circuit 40 is supplied to an H8 board 42. This analog output is amplified by an amplifier 44, filtered through a low-pass filter 46 for rejection of the noise component and converted to a digital signal in an A/D converter 48. The digital signal is then processed with an arithmetic operation processing system comprising a memory 50 and a CPU 52. The H8 board may optionally be connected to a host computer 54. The H8 board 42 also serves as an I/O interface with a Peltier device controller 56. In response to a signal from a thermistor (not shown), the Peltier device controller 56 performs an on-off control over the drive of Peltier devices 19. The CCD circuit may contain a circuit for integrating pixel signals from CCDs. This integrating circuit not only reduces noise but also enables pixel adjustment in the following manner: consider, for example, the case where a CCD produces an output of 125 μm/pix; this output is integrated over 4 pixels to give 500 μm/pix, which is delivered as an adjusted CCD output.

The index-distributed lens array 3, filter 5 and CCD line sensor 7 preferably have the same length. Their length may be the same as the lateral width of the electrophoresis plate 74, or the distance from the left to the right end of the plate 74; alternatively, their length may be slightly shorter than the lateral width of the electrophoresis plate so that it is equal to the distance from the electrophoresis track at the right end to the track at the left end plus an allowance for "smiling".

As described on the foregoing pages, the DNA base sequencer of the present invention uses the fluorescence detecting means which comprises an index-distributed lens array, a filter and a solid-state imaging device such as a CCD line sensor and this design feature not only achieves a considerable reduction in the manufacturing cost of the DNA base sequencer; the sequencer is also capable of efficient and correct detection of fluorescence without the adverse effects of the smiling of tracks during electrophoresis.

What is claimed is:

1. In a DNA base sequencer comprising a flat plate type gel electrophoretic means that has a multiple of tracks for electrophoresing DNA fragments and which is held in a vertical position, a light exciting laser light applying means that applies laser light to the respective tracks in said electrophoretic means from one lateral side thereof in such a way that it crosses said tracks at right angles, and a fluorescence detecting means that detects the fluorescence as generated from the DNA fragments illuminated with the laser light and which converts the detected fluorescence to an electric signal, the improvement wherein said fluorescence detecting means comprises an index-distributed lens array, a filter and a solid-state imaging device.

2. A DNA base sequencer according to claim 1 wherein said index-distributed lens array consists of an upper and a lower row of index-distributed lenses.

3. A DNA base sequencer according to claim 1 wherein said solid-state imaging device is a CCD line sensor.

4. A DNA base sequencer according to claim 1 wherein said fluorescence detecting means comprises, in order from the electrophoretic means side, the index-distributed lens array, the filter and the CCD line sensor.

5. A DNA base sequencer according to claim 4 wherein said CCD line sensor is cooled with Peltier devices.

* * * * *